US011170325B2

(12) United States Patent
Tremblay et al.

(10) Patent No.: US 11,170,325 B2
(45) Date of Patent: Nov. 9, 2021

(54) ADAPTABLE MEDICAL WORKFLOW SYSTEM

(71) Applicant: CareFusion 303, Inc., San Diego, CA (US)

(72) Inventors: Jean-Sebastien Tremblay, Quebec (CA); Sebastien Dumont, Lévis (CA); Ali Dufour, St-Augustin-De-Desmaures (CA); Jean-Francois Lagace, Quebec (CA)

(73) Assignee: CareFusion 303, Inc., San Diego, CA (US)

( * ) Notice: Subject to any disclaimer, the term of this patent is extended or adjusted under 35 U.S.C. 154(b) by 168 days.

(21) Appl. No.: 16/459,540

(22) Filed: Jul. 1, 2019

(65) Prior Publication Data
US 2019/0325543 A1    Oct. 24, 2019

Related U.S. Application Data

(63) Continuation of application No. 12/644,919, filed on Dec. 22, 2009, now abandoned.

(51) Int. Cl.
*G16H 40/20* (2018.01)
*G06Q 10/06* (2012.01)

(52) U.S. Cl.
CPC ............. *G06Q 10/06* (2013.01); *G16H 40/20* (2018.01)

(58) Field of Classification Search
CPC ...................................... G16H 40/20
See application file for complete search history.

(56) References Cited

U.S. PATENT DOCUMENTS 4,857,713 A    8/1989  Brown
6,338,066 B1*  1/2002  Martin .................. G06Q 30/02
                                        707/708
(Continued)

FOREIGN PATENT DOCUMENTS

EP    1443444 A2    8/2004
EP    1443444 A2    8/2004
(Continued)

OTHER PUBLICATIONS

Predicting User Tasks: I Know What You're Doing!; Stumpf et al.; 2005 (Year: 2005).*
(Continued)

*Primary Examiner* — John A Pauls
(74) *Attorney, Agent, or Firm* — Morgan, Lewis & Bockius LLP

(57) ABSTRACT

A system and method for creating a menu for an adapted a medical workflow implemented at a computer coupled to a hospital network is disclosed. The disclosed system and method generates a workflow including a list of predicted medical action options based on an identified healthcare worker and based on a determined operating state or vital state of a patient, creates a menu for displaying the list of predicted medical action options, disables one or more of the predicted medical action options in the menu based on the determined one or more state values associated with an identified medical object, and communicates for display on a graphic interface the menu comprising the disabled one or more predicted medical action options, wherein the disabled one or more predicted medical action options is visible in the menu but unselectable by the healthcare worker.

20 Claims, 10 Drawing Sheets

(56) References Cited

U.S. PATENT DOCUMENTS

| | | | | |
|---|---|---|---|---|
| 2002/0046047 A1* | 4/2002 | Budd | ............. | G16H 50/20 |
| | | | | 705/2 |
| 2002/0143320 A1 | 10/2002 | Levin | | |
| 2002/0178126 A1 | 11/2002 | Beck | | |
| 2003/0050801 A1 | 3/2003 | Ries et al. | | |
| 2004/0169673 A1* | 9/2004 | Crampe | ............. | A61B 34/20 |
| | | | | 715/700 |
| 2005/0086072 A1 | 4/2005 | Fox, Jr. et al. | | |
| 2005/0144043 A1* | 6/2005 | Holland | ............. | G16H 40/67 |
| | | | | 705/3 |
| 2005/0182654 A1 | 8/2005 | Abolfathi | | |
| 2005/0251418 A1 | 11/2005 | Fox, Jr. et al. | | |
| 2006/0106641 A1 | 5/2006 | Bartsch et al. | | |
| 2006/0112050 A1 | 5/2006 | Miikkulainen et al. | | |
| 2006/0175401 A1 | 8/2006 | Roberts | | |
| 2006/0229551 A1 | 10/2006 | Martinez et al. | | |
| 2006/0288095 A1 | 12/2006 | Torok et al. | | |
| 2007/0011108 A1* | 1/2007 | Benson | ............. | G07C 5/008 |
| | | | | 706/8 |
| 2007/0203761 A1 | 8/2007 | Keen | | |
| 2007/0290028 A1 | 12/2007 | Fox et al. | | |
| 2008/0040160 A1 | 2/2008 | Scherpbier et al. | | |
| 2008/0077433 A1 | 3/2008 | Kasprisin et al. | | |
| 2008/0184250 A1 | 7/2008 | Hamadi et al. | | |
| 2008/0270178 A1 | 10/2008 | McRae et al. | | |
| 2008/0306740 A1 | 12/2008 | Schuck | | |
| 2009/0070137 A1 | 3/2009 | Haider et al. | | |
| 2009/0157428 A1 | 6/2009 | Auchinleck | | |
| 2009/0171695 A1 | 7/2009 | Cobbinah et al. | | |
| 2009/0178004 A1* | 7/2009 | Stoval, III | ............. | G16H 10/60 |
| | | | | 715/812 |
| 2009/0228519 A1* | 9/2009 | Purcell | ............. | G06F 11/30 |
| 2010/0198620 A1 | 8/2010 | Mullenger | | |
| 2011/0093279 A1 | 4/2011 | Levine et al. | | |

FOREIGN PATENT DOCUMENTS

| | | | | | |
|---|---|---|---|---|---|
| JP | 2001134706 | * | 5/2001 | ............. | G06Q 30/20 |
| WO | WO 2004/006909 | | 1/2004 | | |
| WO | WO-2004006909 | | 1/2004 | | |

OTHER PUBLICATIONS

"IntelliDOT@ Mother-Baby Breast Milk Matching™: Assuring safety for your tiniest patients checking module", IntelliDOT Corporation, 2008, pp. 1-4.
Australian Examination Report No. 1 for Application No. 2010341599, dated Sep. 29, 2015, 3 pages.
Australian Examination Report No. 1 for Application No. 2016234929, dated May 18, 2018, 5 pages.
Australian Examination Report No. 2 for Application No. 2010341599, dated May 3, 2016, 4 pages.
Australian Examination Report No. 2 for Application No. 2016234929, dated May 10, 2019, 4 pages.
Canadian Office Action for Application No. 2783780, dated Jul. 14, 2017, 8 pages.
Canadian Office Action for Application No. 2783780, dated Jul. 20, 2018, 11 pages.
Canadian Office Action for Application No. 2783780, dated Jun. 25, 2019, 9 pages.
Canadian Office Action for Application No. 2783780, dated Nov. 9, 2016, 5 pages.
Chinese First Office Action for Chinese Application No. 201080058507.2, dated Feb. 25, 2015, 35 pages.
Chinese Office Action for Application No. 201080058507.2, dated Jun. 27, 2016, 3 pages excluding English translation.
Chinese Second Office Action for Application No. 201080058507.2, dated Sep. 2, 2015, 30 pages.
Chinese Third Office Action for Application No. 20180058507.2, dated Feb. 1, 2016, 15 pages excluding translation.
European Extended Search Report Application No. 10843499.4, dated Dec. 20, 2013, 7 pages.
European Office Action for Application No. 10843499.4, dated Dec. 12, 2017, 4 pages.
Halamka et al., "The Security Implications of VeriChip Cloning", JAMIA, vol. 13(6), Nov.-Dec. 2006, pp. 601-607.
Indian Office Action for Application No. 4885/CHENP/2012, dated Mar. 12, 2019, 5 pages.
International Preliminary Report on Patentability for International Application No. PCT/US2010/060860, 5 pages.
International Search Report and Written Opinion for PCT/US2010/060860 dated Jul. 27, 2011 in 9 pages.
Mexican Fourth Office Action for Application No. MX/a/2012/007047, dated Jul. 10, 2015, 24 pages.
Mexican Office Action for Application No. MX/a/2016/009467, dated Feb. 21, 2018, 6 pages excluding machine translation.
Mexican Office Action for Application No. MX/a/2016/009467, dated Jul. 7, 2017, 6 pages excluding machine translation.
Mexican Third Office Action for Application No. MX/a/2012/00747, dated Oct. 31, 2014, 25 pages.
Australian Office Action for Application No. 2019203469, dated Jul. 21, 2020, 6 pages.
Canadian Office Action for Application No. 2783780, dated Jun. 8, 2020, 3 pages.
Australia Office Action for Application No. 2019203469, dated Mar. 5, 2020, 6 pages.
Australian Office Action for Application No. 2019203469, dated Oct. 14, 2020, 6 pages.
Australian Patent Examination Report No. 2 for Application No. 2010341599, dated May 3, 2016, 4 pages.
Mexican Third Office Action for Mexican Application No. MX/a/2012/007047, dated Oct. 31, 2014, 25 pages.
Chinese Third Office Action for Application No. 201080058507.2, dated Feb. 1, 2016, 15 pages excluding translation.
Mexican Office Action for Application No. MW/a/2016/009467, dated Feb. 21, 2018, 6 pages excluding machine translation.
Australian Office Action for Application No. 2019203469, dated Mar. 3, 2021, 8 pages.

\* cited by examiner

ADAPTABLE MEDICAL WORKFLOW SYSTEM

CROSS REFERENCE TO RELATED APPLICATIONS

This application is a continuation application of U.S. application Ser. No. 12/644,919, entitled "ADAPTABLE MEDICAL WORKFLOW SYSTEM," filed on Dec. 22, 2009, the entirety of each of which is incorporated herein by reference.

FIELD

The present disclosure relates to medical workflow systems.

BACKGROUND

The work of a healthcare worker (e.g., a nurse) generally involves performing several tasks related to patient treatment. Often, a healthcare worker performs tasks such as feeding a patient or recording the temperature of a patient using devices such as barcode scanners to enter identities of medications and patients in a medical computer system. During care and treatment of a patient, a healthcare worker may perform several tasks that may collectively be referred to as a "workflow" of the healthcare worker. A healthcare worker may follow a workflow specified by regulation of a healthcare facility. The workflow may be provided by a medical computer system to the healthcare worker on a display screen.

Acceptance of new technologies by a healthcare worker is a problem faced by the healthcare industry. Introduction of a new technology often means some changes to a healthcare worker's workflow and therefore may require efforts on part of the healthcare worker to adopt the new technology. For example, a certain healthcare system configuration may expect a healthcare worker to perform tasks A, B and C, in that order (e.g., scanning a label, administering a medication, documenting a patient's vital signs, etc.). A change or an upgrade to the healthcare system configuration may require the healthcare worker to perform tasks in the order A, C, B or may add an additional task D (e.g., new workflow is A, B, D and C). Such changes in the healthcare system configuration may be disruptive to the workflow that the healthcare worker is used to follow. In some instances, upgrades or changes to existing healthcare configurations may therefore lead to increased errors or reduced efficiency on the part of healthcare workers during the time period in which the healthcare workers become accustomed to the changes.

SUMMARY

Methods and systems that solve the above-discussed and other needs for improved medical workflow are disclosed.

In one aspect of the disclosure, a method of adapting a medical workflow implemented at a processor coupled to a hospital network is disclosed. The method comprises receiving a message comprising medical information data, predicting a healthcare worker's workflow using, at least in part, the medical information data, and communicating to an interface, based on the predicting, a menu comprising one or more medical action options.

In another aspect of the disclosure, a machine-readable medium encoded with instructions for adapting a medical workflow is disclosed. The instructions comprise code to cause a processor to receive a message comprising medical information data, predict a healthcare worker's workflow using, at least in part, the medical information data and communicate to an interface, based on the predicting, a menu comprising one or more medical action options.

In yet another aspect of the disclosure, a system for adapting a medical workflow is disclosed. The system comprises a server; a scanner having an interface and a database. The server comprises a medical information reception section configured to receive a message from the scanner comprising medical information data, a workflow prediction section configured to predict a healthcare worker's workflow using, at least in part, the medical information data and a menu communication section configured to communicate to the scanner, based on the predicted workflow, a menu comprising one or more medical action options for displaying on the interface.

The foregoing and other features, aspects and advantages of the embodiments of the present disclosure will become more apparent from the following detailed description and accompanying drawings.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

The disclosed embodiments address and solve problems related to the aforementioned medical workflow configurations. The embodiments solve these problems, at least in part, by minimizing or eliminating the need for a healthcare worker to follow only a single specific sequence of actions to accomplish certain healthcare tasks. The disclosed embodiments solve these problems, at least by predicting workflow of a healthcare worker based on an identity of a medical item scanned by the healthcare worker. In certain embodiments, workflow prediction is used to create a menu presented to the healthcare worker at a display in response to the healthcare worker's prior actions and menu selections.

According to certain embodiments, the prediction of a workflow is triggered by the act of a healthcare worker scanning a label such as a patient's identification (ID) tag or a medical package label. Using the identity of the scanned medical object, a predictive process at a computer calculates possible next actions by a healthcare worker. Based on the predicted next actions, the computer then directs a display to present a menu to the healthcare worker to facilitate fulfilling the possible next actions. The predictive process adapts based on prior scans performed by the healthcare worker during a session. Therefore, in certain aspects, the predictive process relieves the healthcare worker from having to remember a specific sequence of scanning various medical objects.

Figure 1:
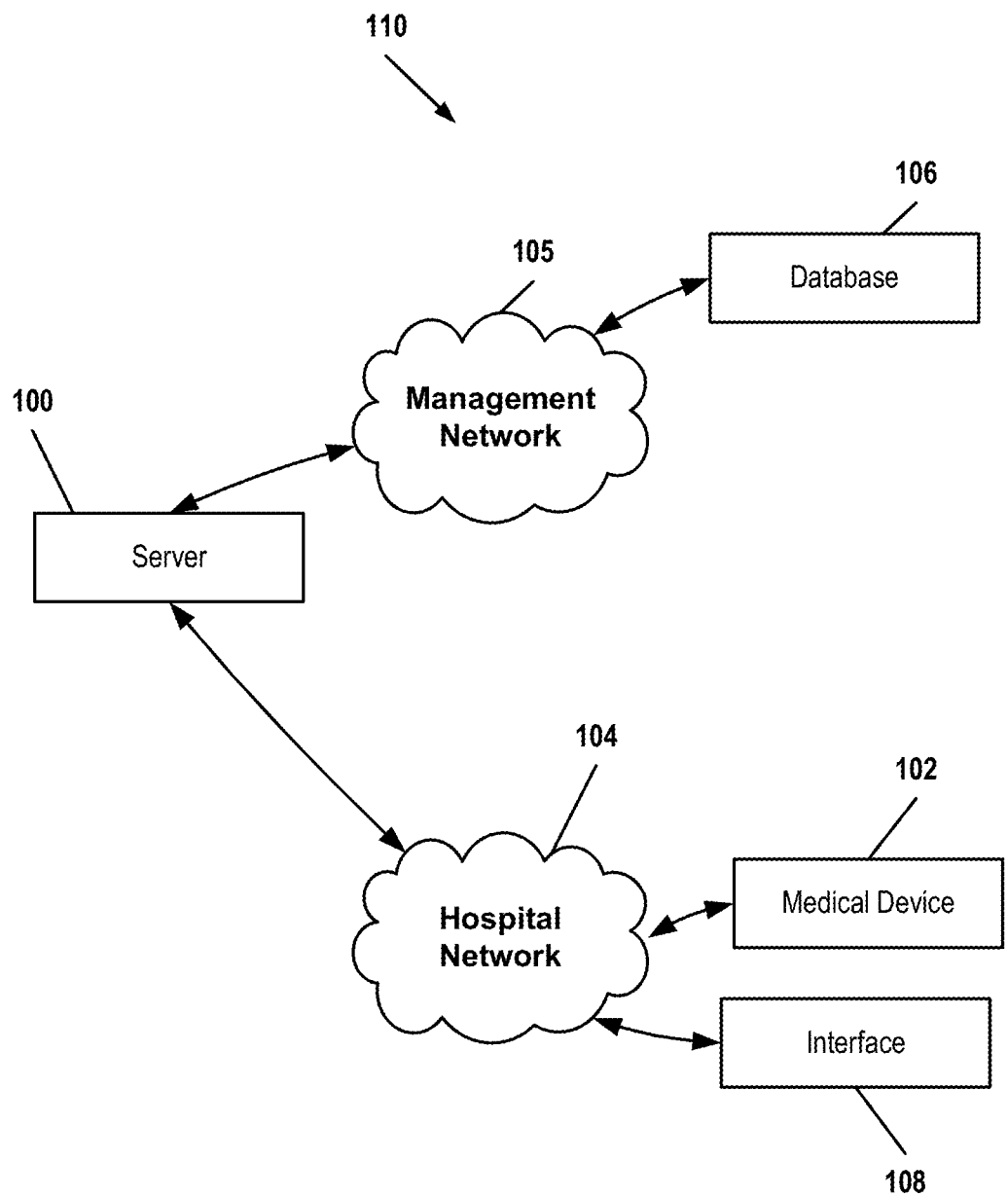
FIG. 1 is a diagrammatic view of a system, in accordance with embodiments of the present disclosure.

FIG. 1 illustrates a simplified diagram of system 110 in accordance with certain configurations of the present disclosure. System 110 includes one or more medical devices 102 capable of communication with a computer server 100 (server) via hospital network 104. System 110 further includes an interface 108 communicatively coupled to server 100. Server 100 communicates to interface 108 for displaying to a healthcare worker. Interface 108 provides a display to a user, as well as an input device for a user to input information into system 110. An example of interface 108 is a touch screen, although in other embodiments, the interface 108 includes a separate display and input device. Interface 108 communicates user interactions (e.g., menu selections) to server 100. In certain embodiments, interface 108 is directly attached to server 100. In certain other embodiments, interface 108 is remotely located, and communicates with server 100 over hospital network 104. In yet other embodiments, interface 108 is integrated into medical device 102.

Still referring to FIG. 1, system 110 further includes medical database 106 communicatively coupled to server 100 through management network 105. Server 100 is configured to predict workflow of a healthcare worker based on the healthcare worker's interaction with medical device 102 and/or interface 108. Server 100 communicates with database 106 to receive or store certain relevant information useful in the prediction of a workflow. By way of illustration and not limitation, in certain configurations server 100 predicts workflow of a healthcare worker using a software application running on a processor of server 100.

Still referring to FIG. 1, by way of illustration and not limitation, medical device 102 may be a computer, a mobile phone, a laptop computer, a thin client device, a personal digital assistant (PDA), a portable computing device, a barcode scanner, a radio frequency identification (RFID) receiver or another device with a processor. As used herein, the terms "scanning," and "scan" refer to a wired or wireless operation of transferring information from an entity to a processor. This includes, for example, barcode scanning by an infrared receiver, sensing of radio frequency identification (RFID) using an RFID antenna, manually reading and entering barcode or patient information to a computer, and so on.

Still referring to FIG. 1, by way of illustration and not limitation, networks 104 and 105 may be, for example, modem connections, a LAN connection including the Ethernet or a broadband WAN connection including DSL, Cable, T1, T3, Fiber Optics, Wi-Fi, or a mobile network connection including GSM, GPRS, 3G, WiMax or other network connections. In certain configurations, hospital network 104 is a dedicated point-to-point link between medical device 102 and server 100 (e.g., a Bluetooth or a wireless USB link).

Figure 2:
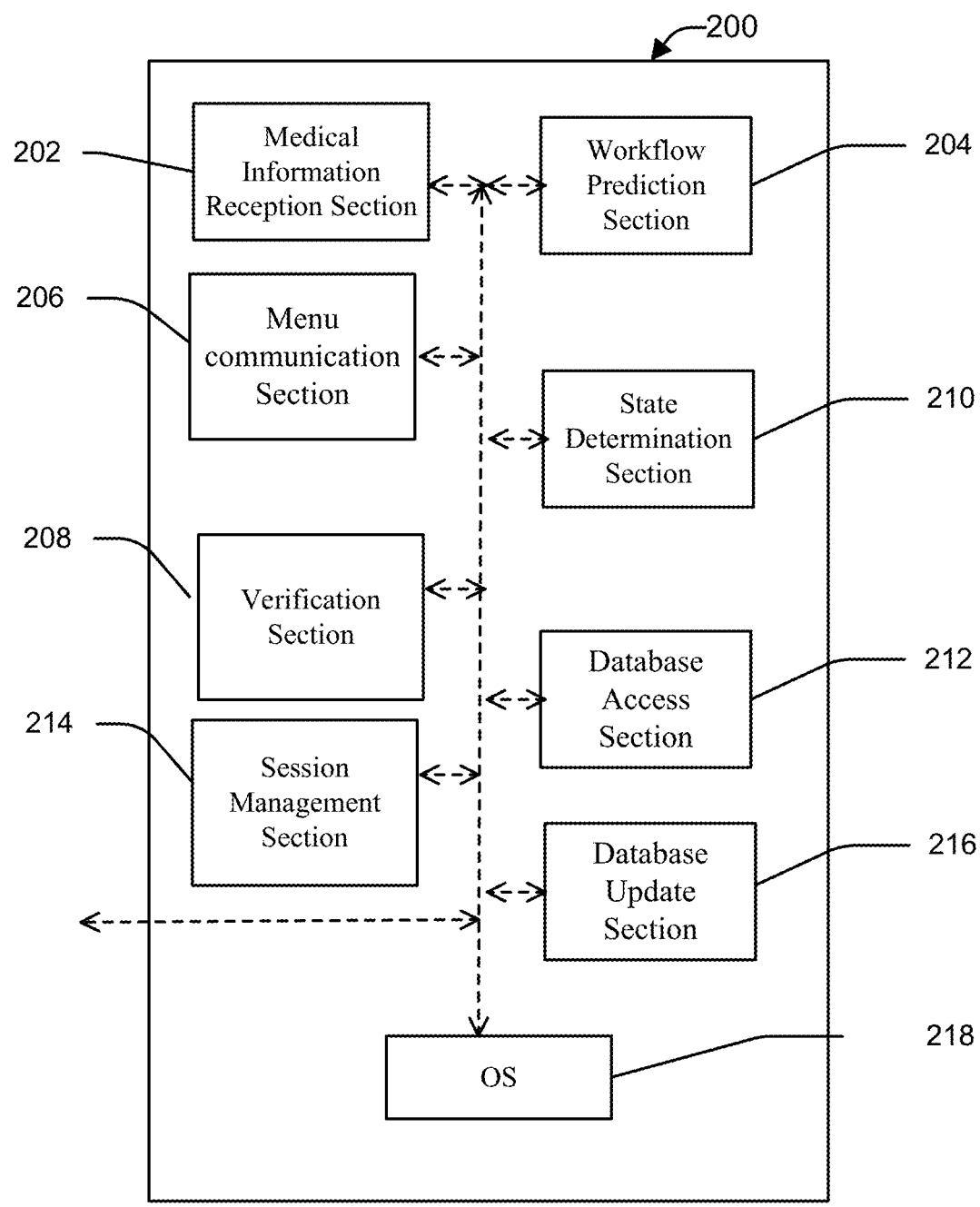
FIG. 2 is a conceptual block diagram of a server, in accordance with embodiments of the present disclosure.

FIG. 2 illustrates a simplified block diagram of configuration 200 of server 100 in accordance with certain configurations of the present disclosure. Operating system (OS) 218 is in communication with a medical information reception section 202, a workflow prediction section 204, a menu communication section 206, a verification section 208, a state determination section 210, a database access section 212, a database update section 216 and a session management section 214. Features and functions of these sections according to certain aspects of the present disclosure may be readily implemented in software, in hardware and/or a combination thereof, and are further described in the disclosure.

Figure 3A:
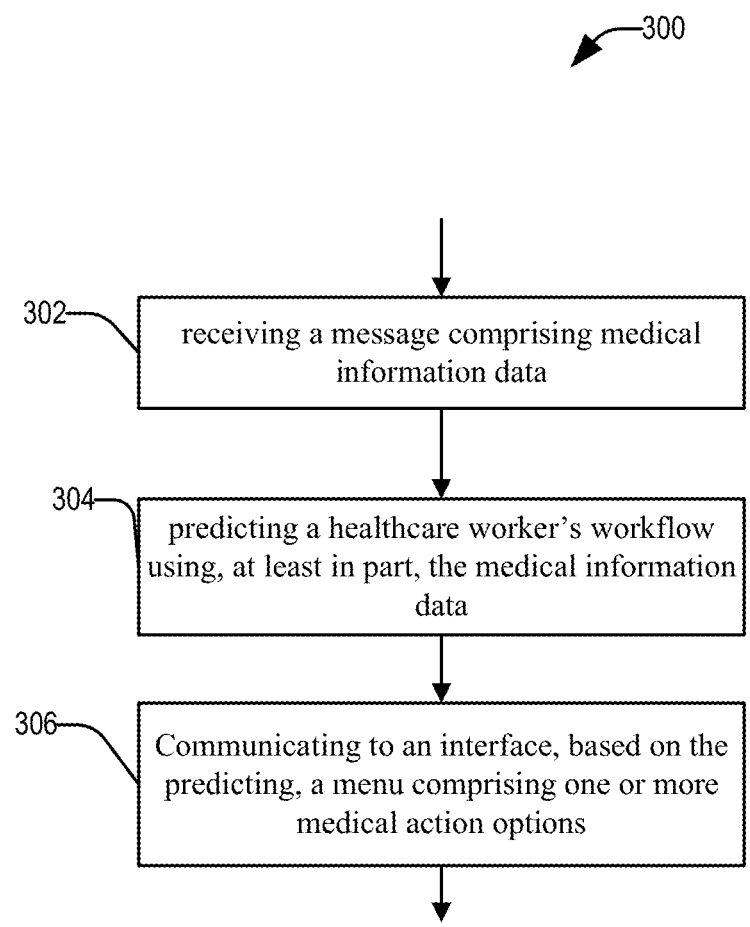
FIG. 3A is a flow chart depicting an exemplary process implemented on a server, in accordance with embodiments of the present disclosure.

FIG. 3A is a flow chart illustrating an exemplary process 300 implemented on server 100, in accordance with certain aspects of the present disclosure. Server 100 is configured to receive messages from medical device 102. Process 300 is initiated by the server 100 receiving a message comprising medical information data in operation 302. In certain configurations, a healthcare worker uses medical device 102 (e.g., a barcode reader) to scan a barcode label or perform a frequency identification (RFID) scan of a medical object. The medical object may be, for example, a medication vial, a food item, a patient's wristband comprising the patient's identity information, and so on. In certain configurations, a healthcare worker directly enters an identity of the medical object into medical device 102 via, for example, a touch screen or a keyboard.

In response to the scan or other input by a healthcare worker, medical device 102 communicates a message comprising certain medical information data to server 100. In certain embodiments, the message is in the form of an internet protocol (IP) packet or any other well-known machine-to-machine communication format. The medical information data includes medical object identification information. For example, the medical information data may include a barcode value or an RFID value that uniquely represents a medical object.

Medical information reception section 202 (FIG. 2) processes the received message carrying the medical information data received by server 100. In certain configurations, medical information reception section 202 parses the received message to extract medical information data. In certain configurations, medical information reception section 202 performs authentication of medical device 102 to ensure that medical device 102 is not a rogue medical device.

Session management section 214 associates a session, based on the medical information received, to the received message. In certain configurations, prediction of a workflow is performed in the context of a session for the workflow. For example, in certain configurations, session management section 214 creates a new session every time a patient ID scan is received or every time a healthcare worker logs in. In certain configurations, workflow prediction process, described in greater detail below, predicts workflow by using one to all messages received during a session to predict a healthcare worker's next action.

Still referring to FIG. 3A, at operation 304, workflow prediction section 204 of server 100 predicts the healthcare worker's workflow using, at least in part, the received medical information data. In certain configurations, workflow prediction section 204 predicts a healthcare worker's workflow based actions possible for the medical object whose identity is communicated in the medical information data. For example, if a scanned medical object is "milk," then workflow prediction section 204 includes in a list of predicted action all possible actions to take for milk, including "feed," "store," and "document feeding" actions. If the scanned medical object corresponds to a patient's wristband, then using the patient's identity, the workflow prediction module 204 predicts the healthcare worker's next possible action (e.g., administer medication to the patient or take the patient's temperature, etc.)

Still referring to FIG. 3A, state determination section 210 determines, based on the identity of the medical object, a state (or states) associated with the scanned medical object. For example, if a scanned medical object is a patient's wristband, state determination section 210 determines if the patient is in a pre-operating state, a post-operating state, an under-observation state, etc. State determination section 210 also obtains information regarding the patient's vitals state (e.g., weight, drug allergies etc.) from database 106. For example, if the scanned medical object is a medication vial, state determination section 210 determines an expiration state (whether medication has expired or not), a recall state (whether there have been any recalls issued for the medication), and so on. State determination section 210 makes the determination regarding states of a scanned medical object by querying database 106 via database access section 212. State determination section 210 determines a state of the scanned medical object by reading state entries and their values associated with the scanned medical object and stored in a memory coupled to server 100 (e.g., database 106). State determination section 210 communicates the retrieved state information to workflow prediction section 204.

Still referring to FIG. 3A, based on state information obtained from state determination section 210 and session information from session management section 214, workflow prediction section 204 predicts next possible actions in the healthcare worker's workflow. In certain configurations, workflow prediction section 204 predicts a single next possible action. Alternatively, in certain other configurations, workflow prediction section 204 predicts multiple levels of next possible actions (e.g., next possible action and the one after that and so on). When needed, workflow prediction section 204 also queries medical database 106 through database access section 212 for establishing a patient's diagnostics needs in order to predict the healthcare worker's workflow. Workflow prediction section 204 also communicates with state determination section 210 to determine a state (or states) associated with the medical object identified in the medical information data received, as previously described.

In certain configurations, the prediction operation 304 comprises a database lookup operation. For example, medical database 106 may include a list of possible operations for a certain medical object (e.g., a medicine) and workflow prediction section 204 may simply use the list associated with the medical object as the predicted next possible action by a healthcare worker. In certain configurations, the prediction operation comprises selecting one of several possible next actions by a healthcare worker, associated with a medical object in medical database 106. In certain configurations, the prediction operation includes using information related to past actions by the healthcare worker (or another healthcare worker having a similar role such as a nurse) and/or the same patient and including these actions in the predicted workflow. Therefore, in certain aspects, workflow prediction section 204 is able to train itself by storing in memory the information about previous workflows and selections by a healthcare worker. In certain configurations, the prediction operation uses prior actions performed by a healthcare worker during the ongoing session to select a next possible action based on the medical object included in the message received in operation 302.

In certain configurations, the prediction operation may associate probabilities with actions possible by a healthcare worker. A probability value associated with a possible next action may be used to prioritize display of the actions in the menu. For example, higher probability actions may be displayed at the top of the menu list, or may be made visibly prominent (e.g., color or font size) to the healthcare worker.

Still referring to FIG. 3A, at operation 306, menu communication section 206 of server 100 communicates, based on the predicted workflow received from workflow prediction section 204, a menu comprising one or more medical action options for displaying to the healthcare worker on interface 108. Various formats are possible for the communication of menu from menu communication section 206 to interface 108. For example, in certain configurations, menu communication section 206 conveys data to be displayed on interface 108 by including display instructions or graphics commands. Such configurations are suitable when interface 108 is embedded in medical device 102 and medical device 102 has a processor capable of receiving graphics commands and displaying a menu to the healthcare worker by decoding the graphics commands. For example, menu communication section 206 may specify display properties such as font, size, color and placement of the menu on interface 108. As an example, in certain configurations, menu communication section 206 uses a well-known technique such as the hypertext markup language (HTML) to specify the menu. Alternatively, in certain configurations, interface 108 is directly connected to server 100 and menu communication section 206 communicates menu to interface 108 using one of several well known graphics peripheral standards such as video graphics array (VGA) and the like.

Still referring to FIG. 3A, in certain configurations, menu communication section 206 includes one or more action items in the predicted workflow, but disables or "grays out" display of the action items so that a healthcare worker may be able to see the action items on the menu, but may not be able to interact with the action item by selecting it from the menu. For example, display menu item for ordering new medication items to re-stock inventory may be grayed out if menu communication section 206 has determined that a sufficient number of doses are available in the inventory. In certain configurations, menu communication section 206 uses one or more operational parameters such as the time of the day, and state values associated with the scanned medical object in making decisions regarding disabling an action item. The grayed out action is displayed to make a healthcare worker aware, for her future reference, that such an action is possible for the scanned medical object.

In certain embodiments, workflow database update section 216 allows updates to database 106, based on a system administrator's input. For example, a system administrator may update workflow database to improve the quality of healthcare provided to patients. A system administrator may update database 106 to adapt "best practices" across several healthcare facilities managed by the system administrator. In certain configurations, updating database 106 includes updating a list of predicted workflows associated with a received medical object ID. In certain configurations, updating database 106 includes adding new patient care rules, such as "do not administer medication X and medication Y together."

Figure 3B:
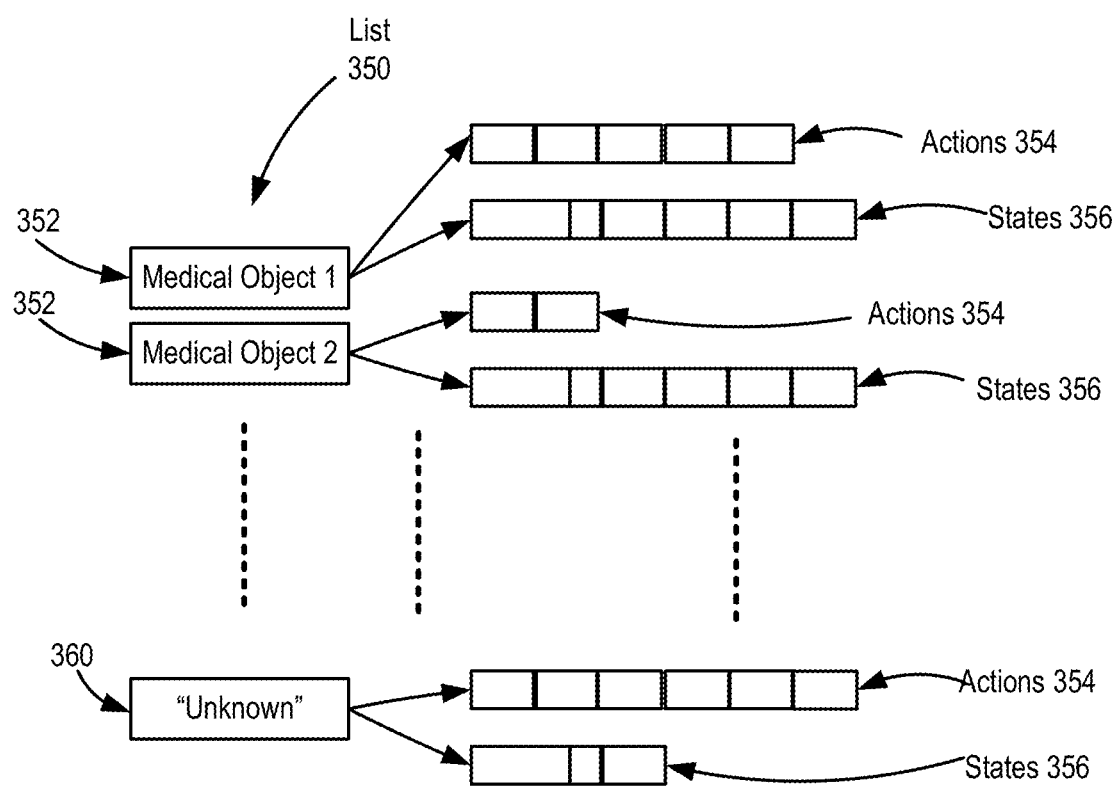
FIG. 3B is a conceptual block diagram depicting entries of a medical database, in accordance with embodiments of the present disclosure.

Referring now to FIG. 3B, a conceptual block diagram of the entries of database 106 is depicted. In certain embodiments, medical database 106 includes a list 350 of a plurality of medical objects 352. For each medical object 352 in the list 350, medical database 106 includes a plurality of possible actions 354 possible for a healthcare worker. Each of the plurality of possible actions 354 has zero or more states 356. In certain configurations, the list 350 of the plurality of medical objects also includes a default entry 360 for an "unknown" medical object.

As an example, list 350 includes medical objects such as "patient," "drug vial," "food item," "IV fluid container," and so on. As an example, possible actions 354 for the entry corresponding to the medical object 352 "drug vial" include "administer," and "discard." As an example, possible actions corresponding to the entry 360 "unknown" include "re-scan," "switch to manual entry," "help," and "contact system administrator." If server 100 cannot recognize a scanned medical object 352, server 100 requests medical device 102 to display the list of possible actions 354 corresponding to the "unknown" entry 360.

Still referring to FIG. 3B, example states 356 associated with the plurality of possible actions 354 include various previously discussed patient states (e.g., pre-operating state, etc.), vital sign states, and so on. In certain configurations, entries of database 106 are static and pre-determined based on rules of the healthcare facility where database 106 is used. In certain configurations, the server 100 updates, from time to time, entries of database 106 and values of state fields 356. For example, the server 100 updates the entries depending on a healthcare worker's previous scans and/or selections.

By way of illustration, and not limitation, the process of adapting a healthcare worker's workflow by predicting the healthcare worker's actions is further illustrated below via an example workflow wherein a healthcare worker feeds milk to a baby patient and documents the feeding in medical records. In particular, two different workflows to perform the "document feeding" task are described below. The workflow illustrated in FIGS. 4A and 4B generally relates to a prior art "static" workflow wherein server 100 is not predicting a healthcare worker's workflow. On the other hand, in the workflow illustrated in FIG. 4C, the server 100 predicts the workflow, based on an identity of a scanned medical object.

Figure 4A:
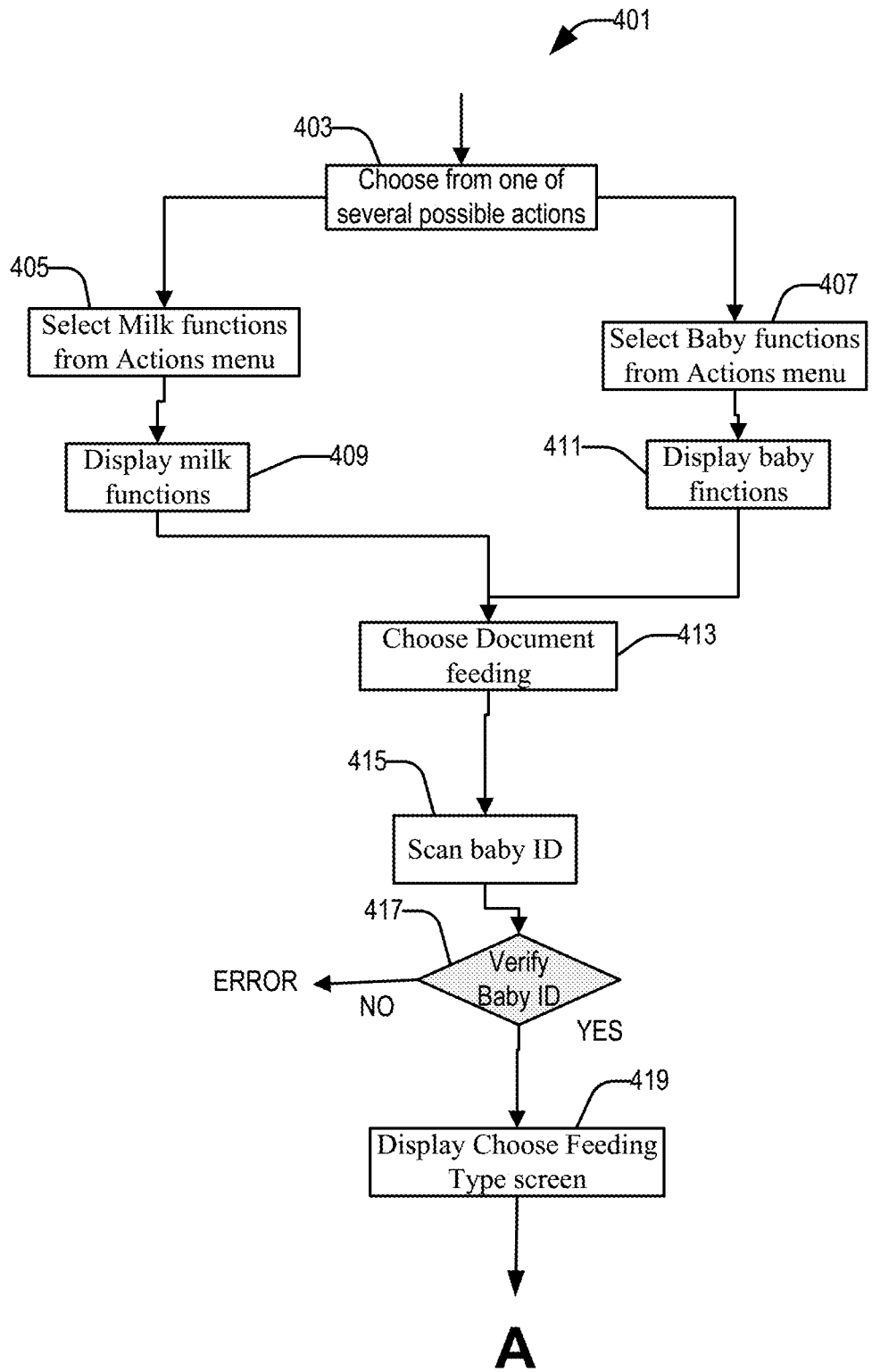
FIG. 4A is a flow chart depicting an exemplary prior art process implemented on a server.

Referring to FIG. 4A, process 401 illustrates an example prior art process related to documenting feeding milk to a baby patient when a medical workflow system is not predicting the workflow. At operation 403, a menu is displayed to a healthcare worker. The menu includes a list of several possible tasks. In general, this list of tasks includes several tasks not pertinent to the current task of documenting a feeding. The healthcare worker chooses from the displayed tasks. Since the healthcare worker intends to document a feeding, the healthcare worker interacts with a "document feeding" workflow. In the document feeding workflow, the healthcare worker chooses milk functions (operation 405) or chooses baby functions (action 407). Based on this selection by the healthcare worker, either a menu of possible milk-related functions is shown to the healthcare worker (operation 409) or a menu of baby functions is displayed to the healthcare worker (operation 411). In response to the displayed menu of milk or baby functions, the healthcare worker indicates, in operation 413, that she wants to document a feeding session. At operation 415, the healthcare worker is prompted for a baby ID. The healthcare worker scans a barcode containing a patient's identification (e.g., a patient bracelet).

As can be seen from the description above of the operations illustrated in FIG. 4A, a healthcare worker cannot simply scan a baby's ID bracelet to begin the "document feeding" workflow. Instead, the healthcare worker has to navigate through multiple menu screens, before she is able to scan a medical object (baby ID).

Still referring to FIG. 4A, at operation 417, a server (not shown in FIG. 4A) verifies the baby ID received at the server. If the scanned baby ID is not valid, an error message is displayed to the healthcare worker. If the scanned baby ID is valid, the server sends a request to a medical device 102 to display "choose feeding type" menu screen in operation 419. In certain configurations, the healthcare worker is given at least three choices: formula feeding, breast feeding or container feeding.

Figure 4B:
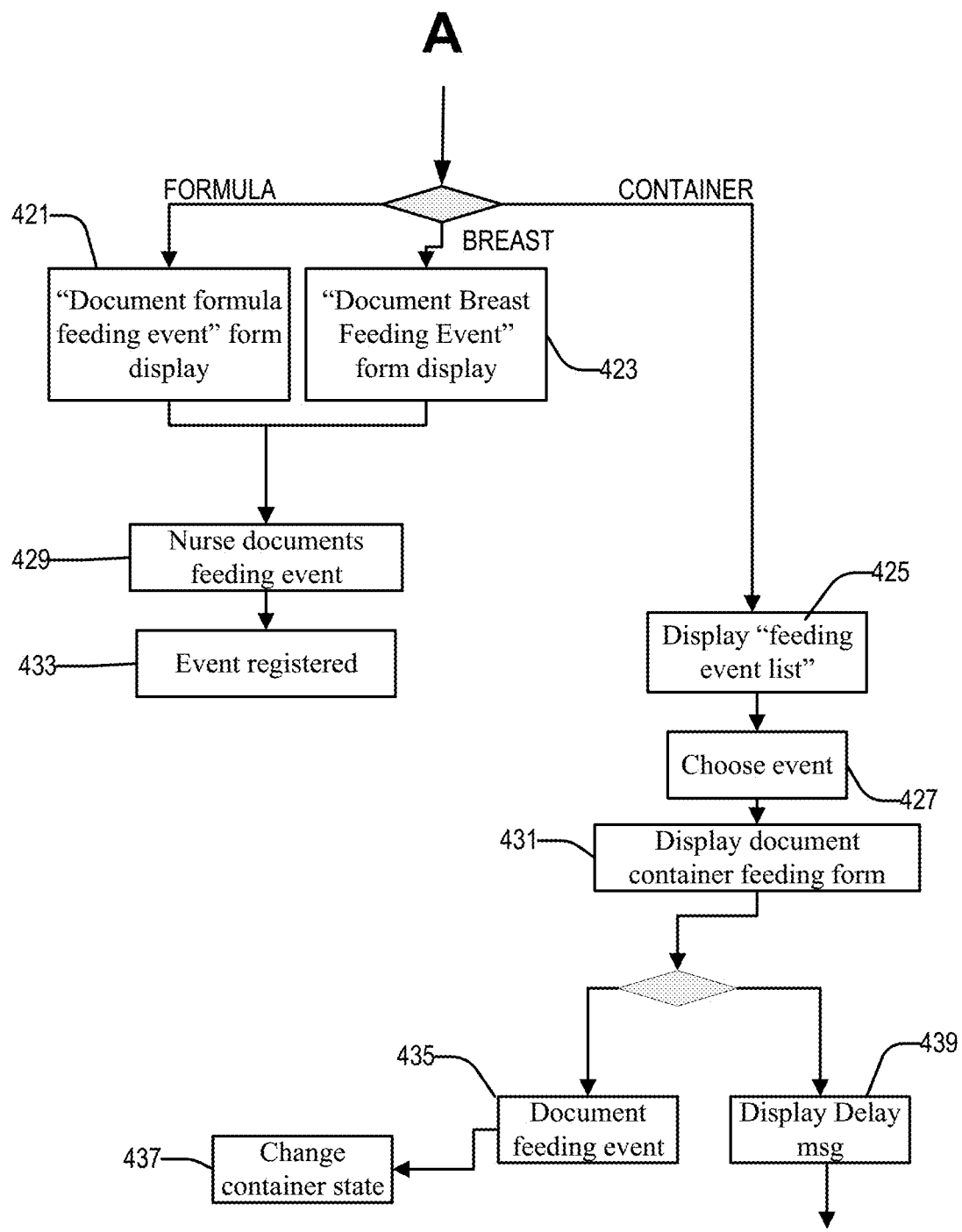
FIG. 4B is a flow chart depicting an exemplary prior art process implemented on a server.

Referring now to FIG. 4B, if the healthcare worker chooses the "formula feeding" option, then a "document formula feeding event" menu screen is displayed to the healthcare worker at operation 421. If the healthcare worker chooses the breast feeding option, then a "document breast feeding event" option is displayed to the healthcare worker at operation 423. If the healthcare worker chooses the container option, then a "feeding events list" option is displayed, at operation 425, to the healthcare worker.

Still referring to FIG. 4B, if "formula feeding" or "breast feeding" event is chosen at operations 421 or 423, the healthcare worker (e.g., a nurse) documents the feeding event in operation 429 by entering pertinent data into a medical device. At operation 433, the server communicates with database 106 and registers the feeding event. If "feeding events list" is chosen at operation 425, then a menu of possible events is displayed to the healthcare worker. At operation 427, the healthcare worker chooses an event from the displayed menu. In response to the selection, server 100 instructs, at operation 431, an interface 108 (not shown in FIG. 4B) to display a form for documenting container feeding. If the delay expected before the documentation is entered (e.g., waiting to finish a typical milk feeding), then the healthcare worker documents the feeding event (operation 435) and the server also causes a state of the container maintained by the server to change at operation 437. If the expected delay before the feeding can be documented has not elapsed, then server 100 causes a delay message to be displayed (operation 439) to the healthcare worker.

Figure 4C:
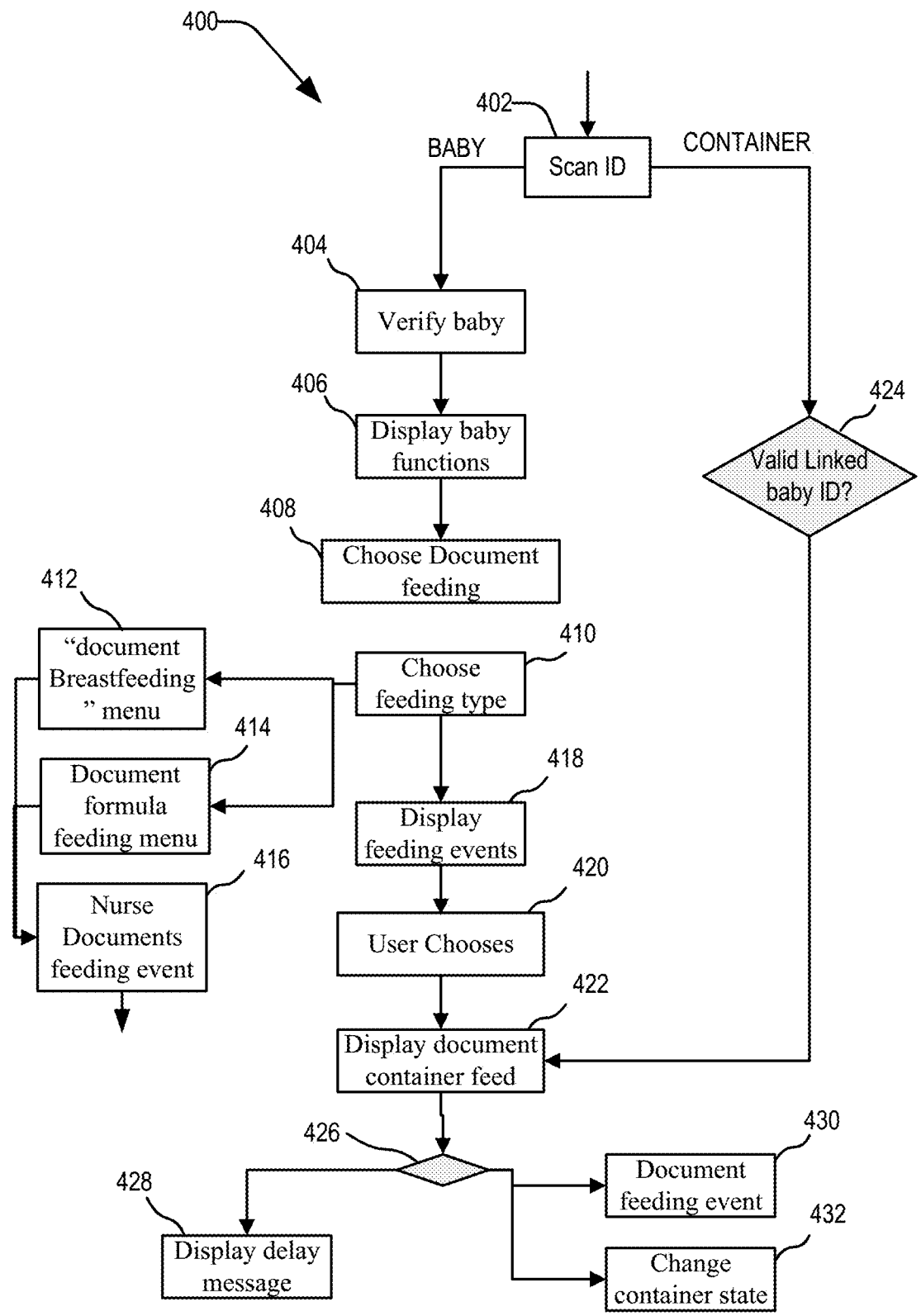
FIG. 4C is a flow chart depicting an exemplary process implemented on a server, in accordance with embodiments of the present disclosure.

FIG. 4C shows exemplary process 400 implemented using the scanner of the present disclosure to predict a healthcare worker's workflow based on identities of scanned medical items. At operation 402, a healthcare worker scans a medical object. For example, the scanned object may be a baby patient's wristband or a milk container. Upon receiving a message comprising medical information data related to the scanned medical object, server 100 verifies the received ID at operation 404. For example, if the scanned ID was for a baby patient, at operation 404, server 100 verifies that the baby patient is a currently admitted patient. If the scanned ID corresponds to a valid baby ID, at operation 406, server 100 sends a message to a medical device 102 to display a menu of baby-related actions to the healthcare worker. For example, one of the actions relates to documenting feeding of milk to the baby patient. The healthcare worker may want to document a milk feeding given to the baby patient in the hospital's medical records and may choose the "document feeding" option at operation 408.

In comparison to process 401 illustrated in FIG. 4A and FIG. 4B, a healthcare worker is able to communicate to server 100 the current task (document feeding) by first scanning a medical object ID. Therefore, process 400 avoids the need for a healthcare worker to navigate through a set of menus before she can communicate to server 100 that the current task (workflow) relates to document feeding of a baby patient.

Still referring to FIG. 4C, at operation 410, server 100 facilitates the display of a "choose feeding type" menu to the healthcare worker by sending a display request to a medical device 102. If the healthcare worker chooses the "breast feeding" menu (operation 412), server 100 communicates a request to medical device 102 to display a workflow menu predicted from "breast feeding a baby" actions. If the healthcare worker chooses "formula feeding" menu (operation 414), server 100 communicates a request to medical device 102 to display a workflow menu predicted from the selection of the "formula feeding" action and patient ID for a baby. Subsequent to either operation 412 or operation 414, the healthcare worker documents the feeding event operation 416.

Still referring to FIG. 4C, if the healthcare worker chooses, at operation 410, the "container feeding" menu, then server 100 predicts possible actions that the healthcare worker may want to perform and, in operation 418, communicates a menu to medical device 102 comprising predicted actions. The healthcare worker may choose, at operation 420, an action from the menu displayed. In response to the healthcare worker's selection at operation 420, server 100 communicates a request to medical device 102 to display, at operation 422, a list of "document container feed" actions. The healthcare worker is also shown a similar message at operation 422, if medical asset ID scanner in operation 402 was that of a container and server 100 was able to link, at operation 424, the scanned container ID with the identity of a baby in the hospital. At operation 426, server 100 checks the expected delay (e.g., duration of feeding milk to a baby patient) has elapsed. If the delay has expired, at operation 430, server 100 facilitates documentation of the feeding event by the healthcare worker. Server 100 updates a medical database coupled to the hospital network, at operation 432, to reflect the feeding. Server 100 then changes a state associated with the container scanned in operation 402 to indicate, for example, that the container has been used. If server 100 decides at operation 426 that a delay has not elapsed, server 100 communicates a message, at operation 428, to a medical device 102 to display a delay message to the healthcare worker.

In comparison to process 401 illustrated in FIG. 4A, process 400 illustrated in FIG. 4C is initiated by a healthcare worker scanning a medical object (e.g., a milk container or a baby patient's wrist ID). Based on the identity of the scanned medical object, server 100 predicts the healthcare worker's workflow and presents menu action items to the healthcare worker. In some aspects, the exact order in which various scans are performed does not matter for a successful execution of a workflow. For example, in process 400, a healthcare worker need not go through multiple menu screens to communicate to server 100 what the healthcare worker wants to accomplish. Instead, the healthcare worker need only scan a baby ID and a milk container, for server 100 to predict the healthcare worker's workflow. Furthermore, the exact order in which the baby ID is scanned and the container ID is scanned does not matter to server 100 supporting the workflow.

It will be appreciated that in certain aspects of the present disclosure, an adaptive workflow method is provided that guides a healthcare worker to a menu of medical tasks by predicting the healthcare worker's workflow from a received barcode scan information. In certain configurations, a medical device communicatively coupled to a server displays a "top level" menu upon starting operation and awaits a barcode scan from the healthcare worker. Upon receiving data related to a barcode scan, the server interprets what has been scanned and displays to the healthcare worker a menu of actions such that it is possible to perform a meaningful medical task with the previously scanned object. The server is configured to accept any barcode format.

In certain configurations, a healthcare worker uses a barcode reader or other device to scan medical objects such as a patient ID, a baby ID or a milk container ID. Based on what was scanned, the system will facilitate the display of next possible tasks to the healthcare worker. In certain configurations, e.g., as described above with respect to FIGS. 1 to 4C, the healthcare worker is a nurse administering milk to a baby. Regardless of the order in which the nurse scans barcodes (e.g., the baby's wristband ID first or the milk container ID first), the server 100 is able to predict that the workflow relates to administering milk to the baby. Based on this prediction, server 100 facilitates presentation of an appropriate medical task menu to the nurse.

FIGS. 5-9 illustrate various display screens displayed on interface 108 to a healthcare worker during accomplishment of medicals tasks by predicting workflows. For example, in certain configurations, interface 108 is a part of a medical device 102 such as a barcode or and RFID scanner. In such configurations, a healthcare worker scans barcode using the medical device 102 and interacts with menu displayed on the interface 108.

Figure 5:
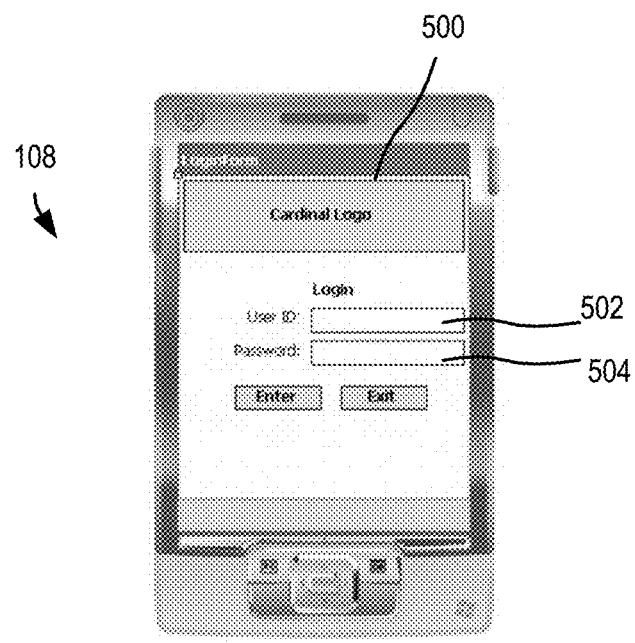
FIG. 5 illustrates a scanner with an exemplary menu screen, in accordance with embodiments of the present disclosure.

FIG. 5 illustrates an exemplary menu screen 500, in accordance with certain aspects of the present disclosure. In certain configurations, medical device 102 displays menu screen 500 to a healthcare worker as an initial login to a predictive workflow scanning application in accordance with various application configurations described above with respect to FIGS. 1 to 4C. Menu screen 500 comprises area 502 where the healthcare enters her user name and further enters a password in area 504. In certain configurations, when a healthcare worker logs in from screen 500, session management section 214 begins a new session for workflow prediction.

Figure 6:
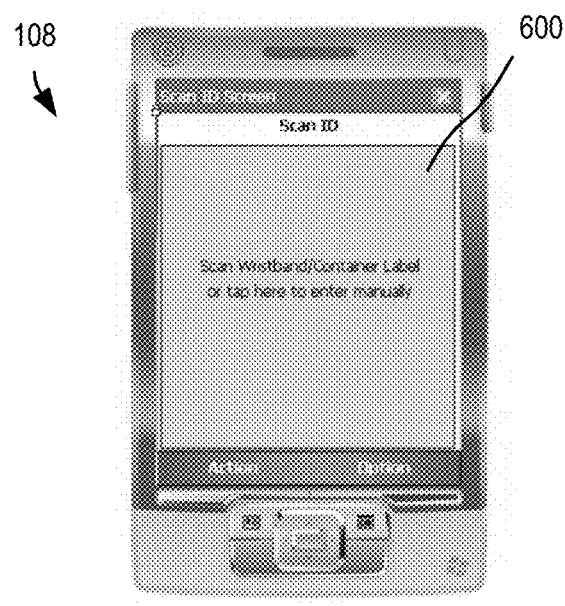
FIG. 6 illustrates a scanner with an exemplary menu screen, in accordance with embodiments of the present disclosure.

FIG. 6 illustrates an exemplary menu screen, in accordance with certain aspects of the present disclosure. Menu screen 600 illustrates a message displayed for a healthcare worker suggesting a next action to perform, based on predictive workflow calculations of the present disclosure. In this case, the suggested actions include scanning a patient's wristband or a medical container label or tapping the interface 108 to receive more possible actions.

Figure 7:
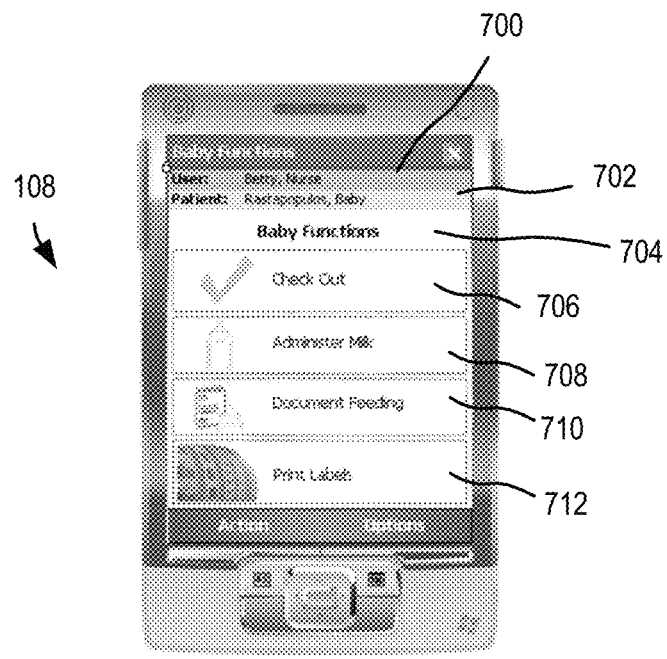
FIG. 7 illustrates a scanner with an exemplary menu screen, in accordance with embodiments of the present disclosure.

FIG. 7 illustrates an exemplary menu screen, in accordance with certain aspects of the present disclosure. Menu screen 700 of interface 108 includes display area 702 displaying a healthcare worker's identity and a patient's identity. Menu screen 700 further includes a list of baby functions, as indicated by a heading display area 704, displaying actions that are possible for a baby patient. Menu screen 700 further comprises a list of actions that the healthcare worker may need to perform, as calculated by predicting the healthcare worker's workflow. The example illustrated in FIG. 7 shows a "baby functions" action in region 704, a "check out task" in region 706, an "administer milk" action in region 708, "document feeding" in region 710 and "print labels" in region 712. Menu screen 700 is an example of a menu that may be presented to a healthcare worker at operation 406 described in FIG. 4C.

Figure 8:
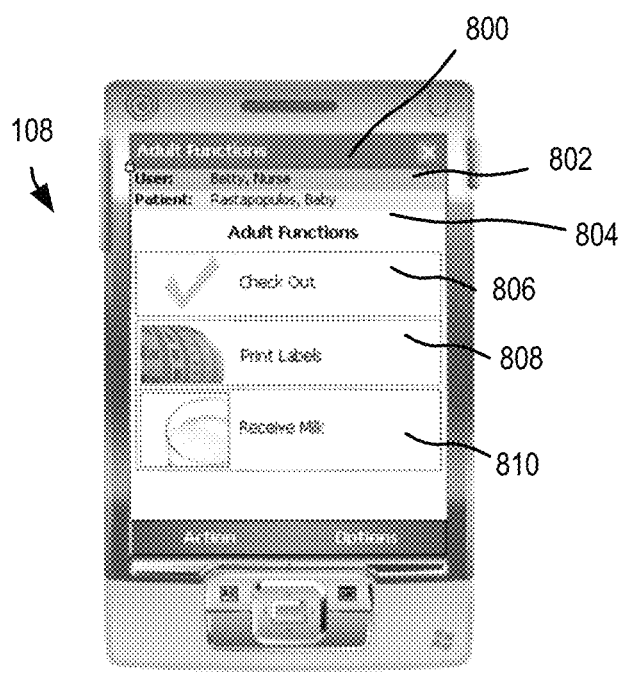
FIG. 8 illustrates a scanner with an exemplary menu screen, in accordance with embodiments of the present disclosure.

FIG. 8 illustrates an exemplary menu screen, in accordance with certain aspects of the present disclosure. Menu screen 800 includes display area 802 displaying a healthcare worker's identity and a patient's identity. Menu screen 800 further includes a list of adult functions, as indicated by a heading display area 804, displaying actions possible for an adult patient. Menu screen 800 further comprises a list of actions that the healthcare worker may need to perform, as calculated by predicting the healthcare worker's workflow. The example illustrated in FIG. 8 shows an "adult functions" action in region 804, a "check out task" in region 806, a "print labels" action in region 808 and a "receive milk" action in region 810.

Figure 9:
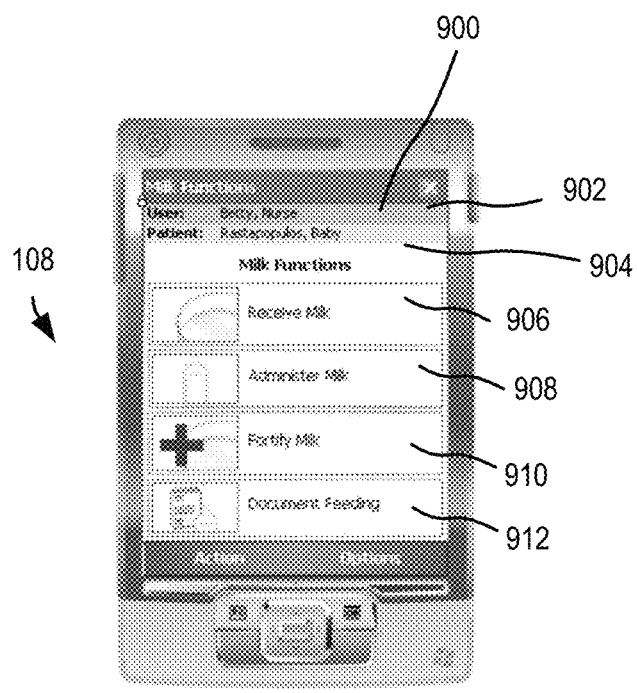
FIG. 9 illustrates a scanner with an exemplary menu screen, in accordance with embodiments of the present disclosure.

FIG. 9 illustrates an exemplary menu screen, in accordance with certain aspects of the present disclosure. Menu screen 900 includes display area 902 displaying a healthcare worker's identity and a patient's identity. Menu screen 900 further includes a list of milk functions, as indicated by a heading display area 904, displaying actions possible for milk (e.g., when a milk container is scanned as a medical object). Menu screen 900 further comprises a list of actions that the healthcare worker may need to perform, as calculated by predicting the healthcare worker's workflow. The example illustrated in FIG. 9 shows a "receive milk" action in region 906 an "administer milk" action in region 908, a "fortify milk" action in region 908, and a "document feeding" action in region 912.

The menu screens 500, 600, 700, 800 and 900 described above with respect to FIGS. 5 to 9 are used at various operations in a workflow for feeding milk to a baby patient. For example, during process 400 illustrated in FIG. 4C, menu screen 700 may be presented at operation 406. Similarly, menu screen 600 may be presented at operation 402.

It will be appreciated that, in certain aspects, workflow prediction techniques described presently, free up a healthcare worker from having to remember a specific sequence of scanning medical objects. The methods and systems of the present disclosure provide for a server in a medical facility to manage menu screens displayed to a healthcare worker in ways that minimize disruption to a healthcare worker's workflow. In certain aspects, the healthcare worker "trains" a system to better predict her next actions, based on her actions during a previous medical workflow. Therefore, configurations of the present disclosure relieve a healthcare worker from having to memorize menu screens and inputs expected from her to accomplish certain healthcare tasks. In certain aspects, workflow prediction is based on IDs of medical objects scanned by a healthcare worker.

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A method of creating a menu for an adapted a medical workflow, the method implemented by a processor coupled to a hospital network, comprising:
   receiving, at a graphic interface, a patient identity of a patient and a healthcare worker identity of a healthcare worker associated with the patient;
   storing menu selections made by the healthcare worker at the graphic interface;
   receiving, based on a scanning of a medical object, a message comprising medical information data that identifies the medical object;
   determining an operating state or a vital state of the patient, and one or more state values associated with the identified medical object;
   predicting medical action options based on the identified healthcare worker and based on the determined operating state or vital state of the patient;
   creating a menu corresponding to the predicted medical action options for the identified healthcare worker based on the predicted medical action options and the healthcare worker's prior menu selections, wherein the creating comprises disabling one or more of the predicted medical action options in the menu based on the determined one or more state values associated with the identified medical object; and
   communicating for display, on the graphic interface, the created menu comprising the disabled one or more predicted medical action options, wherein the disabled one or more predicted medical action options is visible in the menu but unselectable by the healthcare worker.

2. The method of claim 1, wherein generating the predicted medical action options is further based on the healthcare worker's identity and authorization level.

3. The method of claim 1, further comprising:
   starting a session based on a scan of a patient identification or a log in by the healthcare worker; and
   associating session information from the session with the medical information data, wherein generating the predicted medical action options comprises selecting a next action based on prior actions performed by the healthcare worker during the session.

4. The method of claim 1, wherein generating the workflow including the predicted medical action options comprises:
   accessing a workflow database comprising medical action option entries; and
   including at least one of the medical action option entries in the generated workflow.

5. The method of claim 1, wherein the workflow and the predicted medical action options is generated from a workflow database, the method further comprising:
   updating the workflow database based on a system administrator's input.

6. The method of claim 1, wherein the predicted medical action options is generated based on past actions associated with the identified medical object that were performed by one or more healthcare workers having a similar role with the identified healthcare worker.

7. The method of claim 1, wherein the medical information data comprises barcode information.

8. The method of claim 1, wherein the medical information data comprises a medical action selected by the healthcare worker.

9. A non-transitory machine-readable medium encoded with instructions, the instructions comprising code to cause a processor to:
- receive a patient identity of a patient and a healthcare worker identity of a healthcare worker associated with the patient;
- store menu selections made by the healthcare worker at a graphic interface;
- receive, based on a scanning of a medical object, a message comprising medical information data that identifies the medical object;
- determine an operating state or a vital state of the patient, and one or more state values associated with the identified medical object;
- predict medical action options based on the identified healthcare worker and based on the determined operating state or vital state of the patient;
- create a menu corresponding to the predicted medical action options for the identified healthcare worker based on the predicted medical action options and the healthcare worker's prior menu selections, wherein the creating comprises disabling one or more of the predicted medical action options in the menu based on the determined one or more state values associated with the identified medical object; and
- communicate for display on a graphic interface menu comprising the disabled one or more predicted medical action options, wherein the disabled one or more predicted medical action options is visible in the menu but unselectable by the healthcare worker.

10. The machine-readable medium of claim 9, wherein the code for generating the predicted medical action options further comprises code for generating the predicted medical action options based on the healthcare worker's identity and authorization level.

11. The machine-readable medium of claim 9, wherein the medical information data comprises barcode information.

12. The machine-readable medium of claim 9, wherein the predicted medical action options is generated based on past actions associated with the identified medical object that were performed by one or more healthcare workers having a similar role with the identified healthcare worker.

13. The machine-readable medium of claim 9, wherein the instructions further comprise code to cause a processor to:
- start a session based on a scan of a patient identification or a log in by the healthcare worker; and
- associate session information from the session with the medical information data, wherein generating the predicted medical action options comprises selecting a next action based on prior actions performed by the healthcare worker during the session.

14. The machine-readable medium of claim 9, wherein generating the workflow including a predicted medical action options comprises:
- accessing a workflow database comprising medical action option entries; and
- including at least one of the medical action option entries in the generated workflow.

15. The machine-readable medium of claim 14, wherein the instructions further comprise code to cause a processor to update the workflow database based on a system administrator's input.

16. A system, comprising:
a server;
a scanner;
and a database;
wherein the server comprises:
- a medical information reception section configured to receive, from a graphic interface, a patient identity of a patient and a healthcare worker identity of a healthcare worker associated with the patient, and receive a message from the scanner comprising medical information data that identifies a medical object, and store menu selections made by the healthcare worker at the graphic interface;
- a state information determination section configured to determine an operating state or a vital state of the patient, and one or more state values associated with the identified medical object;
- a workflow prediction section configured to predict medical action options based on the identified healthcare worker and based on the determined operating state or vital state of the patient; and
- a menu communication section configured to create a menu corresponding to the predicted medical action options for the identified healthcare worker based on the predicted medical action options and the healthcare worker's prior menu selections, wherein the creating comprises, disabling one or more of the predicted medical action options in the menu based on the determined one or more state values associated with the identified medical object, and communicate for display on a graphic interface the menu comprising the disabled one or more predicted medical action options, wherein the disabled one or more predicted medical action options is visible in the menu but unselectable by the healthcare worker.

17. The system of claim 16, wherein the workflow prediction section is further configured to generate the predicted medical action options based on the healthcare worker's identity and authorization level.

18. The system of claim 16, further comprising:
a session management section configured to:
- start a session based on a scan of a patient identification or a log in by the healthcare worker; and
- associate the session with the medical information data, wherein generating the predicted medical action options comprises selecting a next action based on prior actions performed by the healthcare worker during the session.

19. The system of claim 16, wherein the predicted medical action options is generated based on past actions associated with the identified medical object that were performed by one or more healthcare workers having a similar role with the identified healthcare worker.

20. The system of claim 16, wherein generating the workflow including the predicted medical action options comprises:
- accessing a workflow database comprising medical action option entries; and
- including at least one of the medical action option entries in the generated workflow.

\* \* \* \* \*

UNITED STATES PATENT AND TRADEMARK OFFICE
CERTIFICATE OF CORRECTION

PATENT NO. : 11,170,325 B2
APPLICATION NO. : 16/459540
DATED : November 9, 2021
INVENTOR(S) : Jean-Sebastien Tremblay et al.

Page 1 of 1

It is certified that error appears in the above-identified patent and that said Letters Patent is hereby corrected as shown below:

On the Title Page

IN THE ABSTRACT:
Line 1: Replace "a menu for an adapted a medical" with --a menu for an adapted medical--.

Signed and Sealed this
Twenty-seventh Day of September, 2022

Katherine Kelly Vidal
*Director of the United States Patent and Trademark Office*